United States Patent [19]

Abdulla

[11] 4,264,600
[45] Apr. 28, 1981

[54] TREATMENT OF INFLUENZA WITH 2-ESTERSUBSTITUTED-3,4-DIHYDRO-3-OXOQUINOXALINES

[75] Inventor: Riaz F. Abdulla, Greenfield, Ind.

[73] Assignee: Eli Lilly and Company, Indianapolis, Ind.

[21] Appl. No.: 88,274

[22] Filed: Oct. 25, 1979

Related U.S. Application Data

[63] Continuation-in-part of Ser. No. 60,445, Jul. 25, 1975, abandoned, which is a continuation-in-part of Ser. No. 953,157, Oct. 20, 1978, abandoned.

[51] Int. Cl.³ ............................................. A61K 31/495
[52] U.S. Cl. ...................................... 424/250; 544/354
[58] Field of Search ......................... 424/250; 544/354

[56] References Cited
FOREIGN PATENT DOCUMENTS 1215815 12/1970 United Kingdom .
1308370 2/1973 United Kingdom .
1408675 10/1975 United Kingdom .

OTHER PUBLICATIONS

Baker et al., Chemical Abstracts, 60: 10637g (1963).
Derwent, #25,122, published 12/27/64, #17,295 published 06/24/65.
Kllcwar et al., Chemical Abstracts, 72: 66890n (1968).
Abdulla et al., J. Het. Chem., B pp. 427–432 (1976).
Hurst et al., Buit J. Phaum. 8, 297 (1953).
Westphal, Pharmazie, 32, 687, (1977).
Westphal, Pharmazie, 32, 563, (1977).
Westphal, Pharmazie, 569, (1977).

Primary Examiner—Jerome D. Goldberg
Attorney, Agent, or Firm—James L. Rowe; Arthur R. Whale

[57] ABSTRACT

3,4-Dihydro-3-oxoquinoxalines carrying a carboxylic acid or ester function in the 2 position, used as antiviral agents, particularly against influenza virus, both A and B strains.

9 Claims, No Drawings

TREATMENT OF INFLUENZA WITH 2-ESTERSUBSTITUTED-3,4-DIHYDRO-3-OXOQUINOXALINES

CROSS REFERENCE

This application is a continuation-in-part of my copending application, Ser. No. 60,445 filed July 25, 1979, now abandoned, which was in turn a continuation-in-part of my then copending application Ser. No. 953,157 filed Oct. 20, 1978, now abandoned.

BACKGROUND OF THE INVENTION

Quinoxalines are known which have antiviral or antibacterial action. For example, Acheson, *J. Chem. Soc.* 4731 (1950) reports that p-2'-quinoxalinylaminobenzoyl-(−)glutamic acid had a small growth-inhibitory effect on *L. casei*. The author also prepared 2-(2-diethylaminoethyl)aminoquinoxaline, the corresponding 6,7-dichloro derivative and the corresponding diethylaminopropyl derivative but found that all of these compounds were inactive against *P. gallinaceum* in chicks. 6,7-Dichloro-2-hydroxyquinoxaline-3-carboxylic acid and its ethyl ester were prepared and used as intermediates in the production of these diethylaminoalkylaminoquinoxalines. The same compound was used as an intermediate in the preparation of azeto[1,2-a]quinoxaline-1,3-diones—see Abdulla and Fuhr *J. Het. Chem.*, 13, 427 (1976). Belgium Pat. No. 769,491 (Derwent abstract 4493T supplied) discloses 2,3-dimercaptomethyl quinoxalines in which the benzene ring can be substituted with alkyl, alkoxy, halogen, trifluoromethyl, nitro, or alkylenedioxy. The compounds are said to be antiviral agents. 3,6-Diamino-2-quinoxaline carboxamides, stated to be useful as diuretics, anticonvulsant, antiinflammatory agents, and to have antiviral activity against *Herpes simplex*, are disclosed in U.S. Pat. No. 3,192,212. A group of antiviral quinazolines (isomeric with quinoxalines) are disclosed in Belgium Pat. No. 815,196. A series of antiviral 2-chloro- or 2-hydrazinoquinoxalines are disclosed in three papers by Westphal, et al. *Pharmazie*, 32, 570-571, 687-689, 563-565 (1977). The following types of compounds were prepared: Quinoxaline-2-ones substituted in the 3 position with a heterocyclic ring including benzimidazole, benzothiazole, or benzoxazole (no utility was given for these compounds); 2-chloro or 2-hydrazinoquinoxalines stated to be active against coxsackie B, vaccina, sindbas, and pseudorabies viruses; and, finally, a group of s-triazolo[4,3-a]quinoxalines prepared by cyclizing a 2-hydrazinoquinoxaline, were allegedly useful against some of the above viruses.

In addition to the above listed antiviral agents having the basic quinoxaline structure, there has been a considerable amount of work carried out on quinoxaline-1,4-dioxides as antiviral agents. Much of this work has been summarized in Hurst, et al., *Brit. J. Pharmacol.*, 8, 297, (1953). According to this summary, quinoxaline-1,4-dioxides were the most active compounds tested in experimental psittacosis and lymphogranuloma venereum infections. A large number of derivatives of the quinoxaline-1,4-dioxides are summarized on page 301 of the article and include compounds with the following substituents in the quinoxaline ring: ethyl, ethoxymethyl, acetyoxymethyl, 2-methyl-3-ethyl, 2-methyl-3-carboethoxy, 2,3-dihydroxymethyl, 2,3-diiodomethyl, 2,3-bis(dimethylaminomethyl), etc. Substituents in the benzene ring include: halogens, alkyl, nitro, trifluoromethyl, cyano, carboethoxy, carbamyl, acetamido, etc. (see also Derwent Abstract 5641U abstracting U.K. Pat. No. 1,305,138). A similar group of quinoxaline-1,4-dioxides are disclosed in Belgian Pat. No. 683,206, abstracted as Derwent No. 25,122. Substituted 2-formyl-quinoxaline-1,4-dioxides are disclosed in U.S. Pat. No. 3,433,871. The compounds are said to be antibacterial and antiviral compounds. U.K. Pat. No. 1,308,370 discloses an improved method of making substituted quinoxaline-1,4-dioxides having a variety of substituents in the quinoxaline ring including carboxamides (page 13), esters (page 15), a third ring (page 17-21), acyl derivatives (page 21), 3-hydroxy-2-alkoxy carbonyl derivatives (page 23), hydroxy carboxamides (page 24), etc. These compounds are alleged to have in vitro activity against harmful micro-organisms. Antiviral activity is not mentioned. Another patent relating to methods of preparing quinoxaline-1,4-dioxides, is U.K. Pat. No. 1,215,815. Page 1 of this patent reviews the literature briefly. 2-Hydroxy-3-carboalkoxyquinoxaline-1,4-dioxides are named specifically. Finally, U.S. Pat. No. 3,957,387 describes a group of carboxmidoquinoxalinedioxides. The compounds are alleged to be antibacterial substances.

The above survey of antiviral quinoxalines or quinoxalines containing various substituent groups and useful as either antiviral or antibacterial agents is not exhaustive and merely exemplary of the volumninous literature on the subject. It should be noted, however, that there has not been any disclosure of quinoxalines having antiviral activity, particularly against both Maryland B and Ann Arbor strains of influenza virus in vivo.

DESCRIPTION OF THE INVENTION

This invention provides a method of treating viral infections in mammals with 3,4-dihydro-3-oxoquinoxalines having an ester or acid group at C-2 of the following formula:

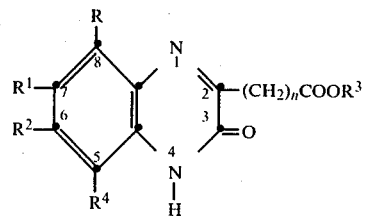

wherein R and $R^4$ are individually H, $NO_2$ or MeO; $R_1$ and $R^2$ are individually H, $NO_2$, MeO or halo such that at least one of R, $R^1$, $R^2$ and $R^4$ is other than H, such that if neither $R^1$ nor $R^2$ is $NO_2$ or MeO, both $R^1$ and $R^2$ are individually halo and both R and $R^4$ are H, and such that one of $R^1$ and $R^2$ is MeO only if one of R, $R^1$, $R^2$ and $R^4$ is nitro; $R^3$ is $C_1$–$C_4$ alkyl, $C_3$–$C_6$ cycloalkyl, $C_3$–$C_4$ alkenyl, H or 2-chloroethyl; and n is 0 or 2. Pharmaceutical compositions for use in in vivo treatment of viral infections are also provided. This invention also provides a method for killing viruses in vitro by applying a compound of the above formula to a viral habitat.

Compounds coming within the scope of the above formula are prepared by reacting a suitably substituted o-phenylenediamine with a dialkyl 2-ketomalonate (a dialkyl mesoxalate) when n is 0 or a dialkyl 2-ketoglutarate when n is 2. The reaction is carried out in a mutual anhydrous solvent, customarily at reflux temperature of the solvent and is illustrated below in the following reaction scheme:

REACTION SCHEME 1

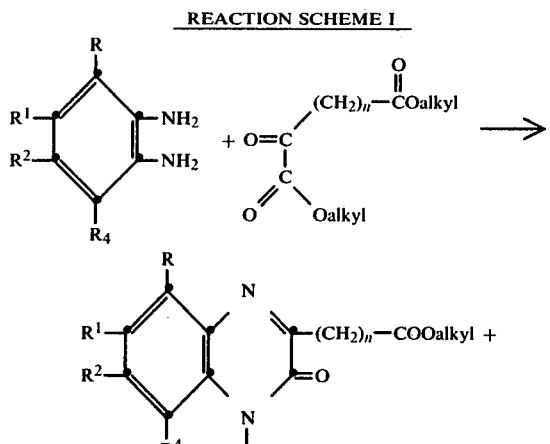

According to Reaction Scheme I, if R and $R^4$ are hydrogen and $R^1$ and $R^2$ are the same substituent; i.e., Cl, or Br, for example, only one product (represented by either II or III) will result, but if the starting o-phenylenediamine is unsymmetrically substituted, i.e., R or $R^4$ is other than hydrogen or $R^1$ and $R^2$ are not identical, a mixture of isomeric products will result as represented by formulas II and III. The various ester groups which $R^3$ represents can be incorporated in the 3,4-dihydro-3-oxoquinoxalines in one of two ways. First, the initial reactant, the mesoxalate, can be esterified with $C_1-C_4$ alkyl groups (corresponding to Formula I wherein $R^3$ is $C_1-C_4$ alkyl) or other groups represented by $R^3$. Thus, in the final product, whether it be formula II or III, the ester group would be the same as that present in the starting material. Secondly, the alkyl ester of Formula II or III can be hydrolyzed to yield the free acid (those compounds of Formula I in which $R^3$ is H) and this free acid can in turn be reesterified with a $C_3-C_6$ cycloalkyl group, a $C_3-C_4$ alkenyl group or a $C_1-C_4$ alkyl group.

In the above reaction scheme, when $R^1$ and $R^2$ are different groups, the product of the reaction of the substituted o-phenylenediamine and diethyl mesoxalate is a mixture of compounds represented by formulas II and III above. A reaction procedure for the unequivocal synthesis of a given compound coming within the scope of this invention in which n is 0 is illustrated in Reaction Scheme 2 below:

Reaction Scheme 2

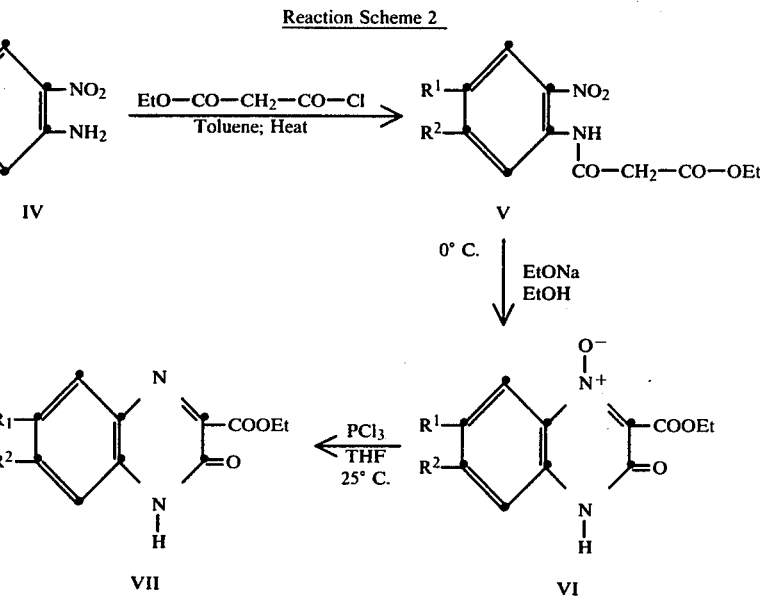

in which $R^1$ and $R^2$ have their previously assigned meaning.

According to Reaction Scheme 2, a 2-nitro-4,5-disubstituted aniline (IV) is reacted with ethyl malonyl chloride (or other alkyl malonyl halide) to give the corresponding ethyl malonyl amide derivative on the aniline nitrogen (V). A base catalyzed annelation using sodium ethoxide at 0° C. yields the quinoxaline $N^1$-oxide (VI), treatment of which with phosphorus trichloride in tetrahydrofuran (THF) at ambient temperature produces unambiguously a 6,7-disubstituted-3,4-dihydro-3-oxo-2-quinoxaline carboxylate, ethyl ester (VII).

Compounds preparable by the above procedures include the following:

n-propyl 6-iodo-7-chloro-2,3-dihydro-3-oxo-2-quinoxaline carboxylate,
n-propyl 6-chloro-7-iodo-2,3-dihydro-3-oxo-2-quinoxaline carboxylate,
methyl 6,7-dichloro-2,3-dihydro-3-oxo-2-quinoxaline propionate,
8-nitro-2,3-dihydro-3-oxo-2-quinoxaline carboxylic acid,
6-fluoro-7-bromo-2,3-dihydro-3-oxo-2-quinoxaline carboxylic acid,

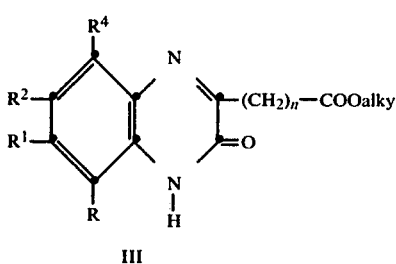

allyl 6-fluoro-7-nitro-2,3-dihydro-3-oxo-2-quinoxaline propionate, methyl 7-methoxy-8-nitro-2,3-dihydro-3-oxo-2-quinoxaline carboxylate, n-butyl 6-iodo-7-nitro-2,3-dihydro-3-oxo-2-quinoxaline carboxylate, isobutyl 7-nitro-8-chloro-2,3-dihydro-3-oxo-2-quinoxaline carboxylate, methallyl 6,7-difluoro-2,3-dihydro-3-oxo-2-quinoxaline propionate.

The above compounds are particularly useful in treating or preventing viral infections caused by influenza virus in vivo. Infection caused by Maryland B and Ann Arbor strains, representative of the A and B strains of the virus, of influenza viruses are treatable by compounds according to formula I. A particular subgroup of very active agents against influenza infections in vivo are compounds of the following structure:

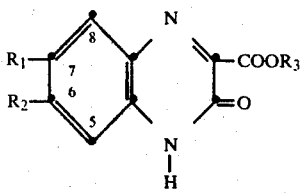

in which $R^1$ and $R^2$ are halogen or one of $R^2$ and $R^1$ is nitro and the other is H and $R^3$ is $C_1$–$C_4$ alkyl, preferably methyl or ethyl. Particularly active antiviral agents represented by Formula X include:

ethyl 6,7-difluoro-3,4-dihydro-3-oxo-2-quinoxaline carboxylate ethyl 6,7-dichloro-3,4-dihydro-3-oxo-2-quinoxaline carboxylate ethyl 6,7-dibromo-3,4-dihydro-3-oxo-2-quinoxaline carboxylate ethyl 6,7-diiodo-3,4-dihydro-3-oxo-2-quinoxaline carboxylate ethyl 6-chloro-7-bromo-3,4-dihydro-3-oxo-2-quinoxaline carboxylate ethyl 6-bromo-7-chloro-3,4-dihydro-3-oxo-2-quinoxaline carboxylate ethyl 7-nitro-3,4-dihydro-3-oxo-2-quinoxaline carboxylate.

The preparation of the above compounds is illustrated by the following specific examples:

EXAMPLE 1

Preparation of Ethyl 6,7-Dichloro-3,4-dihydro-3-oxo-2-quinoxaline Carboxylate A solution of 17.7 g. of 4,5-dichloro-o-phenylenediamine and 200 ml. of anhydrous ethanol was prepared. A 17.4 g. batch of diethyl 2-keto-malonate was added to this solution and the mixture was heated to refluxing temperature for about 17 hours. The volatile constituents were removed by evaporation in vacuo. Recrystallization of the residue from ethanol yielded 20 g. of ethyl 6,7-dichloro-3,4-dihydro-3-oxo-2-quinoxaline carboxylate formed in the above reaction; melting in the range of 226°–227° C.

EXAMPLE 2

Preparation of Ethyl 6-Chloro-7-bromo-3,4-dihydro-3-oxo-2-quinoxaline Carboxylate Five grams of 2-nitro-4-bromo-5-chloroaniline were dissolved in 150 ml. of benzene. Five grams of the acid chloride of monoethyl malonate were added with stirring under a nitrogen atmosphere. The reaction mixture was heated to refluxing temperature overnight. Thin-layer chromatography indicated that the reaction was essentially complete at this time. The reaction mixture was cooled and the benzene removed by evaporation in vacuo. The residue containing N-ethoxycarbonylacetyl 2-nitro-4-bromo-5-chloro)aniline formed in the above reaction, was recrystallized from anhydrous ethanol to yield fluffy yellow crystals melting at 119°–121° C.

Sodium ethoxide was prepared under anhydrous conditions from 35 ml. of anhydrous ethanol and 1 g. of sodium in a nitrogen atmosphere. The mixture was stirred until the sodium was dissolved completely after which time the mixture was chilled to about 0° C. N-ethoxycarbonylacetyl 2-nitro-4-bromo-5-chloroaniline was added and the resulting mixture was stirred at 0° C. for about 3 hours. The reaction was then quenched by adding it to 300 ml. of 1 N aqueous hydrochloric acid at 0° C. This aqueous mixture was stirred until a solid precipitate formed. The precipitate was separated by filtration, dried, and the filter cake was recrystallized from anhydrous ethanol. Ethyl 6-chloro-7-bromo-3-oxo-2-quinoxaline carboxylate N-oxide thus prepared melted at 219°–221° C.; yield=2 g.

Analysis Calc.: C, 38.01; H, 2.32; N, 8.06. Found: C, 37.79; H, 2.35; N, 8.24.

One gram of ethyl 6-chloro-7-bromo-3,4-dihydro-3-oxo-2-quinoxaline carboxylate N-oxide was dissolved in 50 ml. of THF. Six ml. of phosphorus trichloride were added and the resulting mixture heated gently at refluxing temperature overnight. The reaction mixture was poured into 500 ml. of an ice-water mixture. A solid, comprising ethyl 6-chloro-7-bromo-3,4-dihydro-3-oxo-2-quinoxaline carboxylate formed in the above reaction, was separated by filtration; melting point=203°–205° C.; yield=0.6 g.

EXAMPLE 3

Preparation of Ethyl 6,7-Difluoro-3,4-dihydro-3-oxo-2-quinoxaline Carboxylate About 25 ml. of acetic anhydride were added cautiously to 25.8 g. of 3,4-difluoroaniline. The mixture was stirred for 1 hour after the addition was complete and was then poured over ice. The resulting white precipitate comprising 3,4-difluoroacetanilide was separated by filtration, and dried. Recrystallization from a benzene-acetone solvent mixture yielded 30 g. of 3,4-difluoroacetanilide melting at 125°–6° C.

Analysis Calc.: C, 56.14; H, 4.12; N, 8.12. Found: C, 56.28; H, 4.22; N, 8.16.

A solution of 8.5 g. of 3,4-difluoroacetanilide was prepared in 50 ml. of 18 M sulfuric acid, and was chilled to about 0° C. A 10.5 g. portion of propyl nitrate was added in dropwise fashion. The consequent reaction mixture was stirred at about 0° C. for two hours and was then poured over an ice-water mixture. A pale yellow precipitate comprising 4,5-difluoro-2-nitroacetanilide formed in the above reaction was separated by filtration. The filter cake was washed several times with water and then recrystallized from an ethanol-water solvent mixture (yield=9 g.). The compound melted at 105°–107° C.

Analysis Calc.: C, 44.46; H, 2.80; N, 12.96. Found: C, 44.24; H, 2.76; N, 12.88.

A mixture of 6.51 g. of 4,5-difluoro-2-nitroacetanilide and 100 ml. of 6 N aqueous hydrochloric acid was heated to refluxing temperature for about 2 hours. The reaction mixture was then cooled. Crystals which formed were separated by filtration, and the separated crystals were washed with water, dried, and recrystallized from a hexane-dichloromethane solvent mixture. A yield of 5.0 g. of 4,5-difluoro-2-nitroaniline was obtained, melting at 106°–108° C.

Analysis Calc.: C, 41.39; H, 7.32; N, 16.07. Found: C, 41.41; H, 7.35; N, 15.85.

A reaction mixture was prepared containing 8.75 g. of 4,5-difluoro-2-nitroaniline, 200 ml. of ethanol, and as a catalyst 1 g. of 10 percent palladium-on-carbon. The mixture was hydrogenated until the theoretical amount of hydrogen had been absorbed, using a low-pressure hydrogenation apparatus. The catalyst was separated by filtration using standard precautions and the product of the reaction, 4,5-difluoro-o-phenylenediamine, was reacted with diethyl mesoxalate following the procedure of Example 1 without further purification. The product of this reaction, ethyl 6,7-difluoro-3,4-dihydro-3-oxo-2-quinoxaline carboxylate, melted at about 193°–195° C.

EXAMPLE 4

Preparation of 6,7-Difluoro-3,4-dihydro-3-oxo-2-quinoxaline Carboxylic Acid

To 2.42 g. of ethyl 6,7-difluoro-3,4-dihydro-3-oxo-2-quinoxaline carboxylate were added 50 ml. of 2 N aqueous sodium hydroxide. The mixture was heated to refluxing temperatures for 3 hours and was then treated with charcoal, cooled, and filtered. The filtrate containing 6,7-difluoro-3,4-dihydro-3-oxo-2-quinoxaline carboxylic acid formed in the above reaction was acidified with 12 N aqueous hydrochloric acid. The acid, being insoluble in the aqueous acidic mixture, precipitated and the precipitate was separated by filtration. The filter cake was crystallized from an ethanol-acetone solvent mixture to yield 1.3 g. of 6,7-difluoro-3,4-dihydro-3-oxo-2-quinoxaline carboxylic acid melting at 220°–225° C.

Analysis Calc.: C, 47.80; H, 1.78; N, 12.39. Found: C, 47.73; H, 1.94; N, 12.63.

EXAMPLE 5

Preparation of Ethyl 6,7-Diiodo-3,4-dihydro-3-oxo-2-quinoxaline Carboxylate

A reaction mixture was prepared containing 76 g. of 20% oleum, 10 g. of iodine and 10 g. of o-dinitrobenzene. The reaction mixture was stirred at a temperature in the range 170°–175° C. for 2 hours and was then cooled. The cooled reaction mixture was poured onto ice and then filtered. The filter cake, comprising 1,2-dinitro-4,5-diiodobenzene formed in the above reaction, was dissolved in 1 l. of ether. The ether solution was washed with aqueous bisulfite and saturated aqueous sodium bicarbonate, and then dried. The ether was removed therefrom in vacuo, and the crude solid residue crystallized from ethanol to yield brownish plates consisting of 1,2-dinitro-4,5-diiodobenzene melting at 177°–178° C.

A solution was prepared from 3 gms. of 1,2-dinitro-4,5-diiodobenzene in 150 ml. of ethanol. Gaseous ammonia was passed into the solution while heating to refluxing temperature. This procedure was continued until TLC indicated that all starting material had reacted (about 8 hours). The volume of the solution was then reduced to ⅓ of the original volume and the solution was cooled. 2-nitro-4,5-diiodoaniline formed in the above reaction precipitated and was collected by filtration; mp=196°–7° C.; yield=1.70 g.

Analysis Calc.: C, 18.48; H, 1.03; N, 7.18. Found: C, 18.65; H, 1.08; N, 7.33.

A reaction mixture was prepared from 1.2 g. of 2-nitro-4,5-diiodoaniline, 1.8 g. of stannous chloride and 10 ml. of 12 N aqueous hydrochloric acid. The reaction mixture was heated to a temperature in the range 80°–100° C. with stirring. The original deep yellow color of the solution was soon discharged. After 2 hours of heating and stirring, the reaction mixture was dumped into a mixture of 100 ml. of water and 25 ml. of aqueous sodium hydroxide. A tan solid consisting of 4,5-diiodo-o-phenylenediamine precipitated and was collected by filtration; yield=0.9 g.

A solution was prepared from 0.9 g. of 4,5-diiodo-o-phenylenediamine and 25 ml. of ethanol. Five grams of diethyl ketomalonate were added and the resulting mixture was heated to refluxing temperature with stirring overnight. The reaction mixture was then cooled. Ethyl 6,7-diiodo-3,4-dihydro-3-oxo-2-quinoxaline carboxylate formed in the above reaction precipitated and was collected by filtration; yield=0.8 g.; mp=275°–276° C.

Analysis Calc.: C, 28.09; H, 1.70; N, 5.96. Found: C, 28.01; H, 1.72; N, 6.07.

EXAMPLE 6

Hydrolysis of Ethyl 6,7-Dichloro-3,4-dihydro-2-oxo-3-quinoxaline Carboxylate One gram of ethyl 6,7-dichloro-3,4-dihydro-2-oxo-3-quinoxaline carboxylate was dissolved in a mixture of 25 ml. of isopropanol and 75 ml. of water. Five grams of potassium hydroxide were added and the resulting mixture heated to reflux temperature for 5 minutes. The hot reaction mixture was decolorized with activated charcoal and filtered. The filtrate was acidified with 12 N aqueous hydrochloric acid. Needle-like yellow crystals precipitated comprising 6,7-dichloro-3,4-dihydro-2-oxo-3-quinoxaline carboxylic acid formed in the above hydrolysis, m.p.=above 300° C. The acid was collected by filtration.

EXAMPLE 7

Preparation of esters 6,7-Dichloro-3,4-dihydro-3-oxo-2-quinoxaline carboxylic acid prepared from the corresponding ethyl ester by the procedure of Example 6 was esterified with methanol according to the following procedure: Two grams of the free acid and 20 ml. of anhydrous methanol were mixed with a catalytic quantity of boron trifluoride etherate dissolved in methanol. The mixture was heated to refluxing temperature for 60 hours after which time it was cooled and filtered. Methyl 6,7-dichloro-3,4-dihydro-3-oxo-2-quinoxaline carboxylate separated and was isolated by filtration; weight=153 g.; color=greenish yellow; mp=258°-260° C.

EXAMPLE 8

Alternate ester preparation

One gram 6,7-dichloro-3,4-dihydro-3-oxo-2-quinoxaline carboxylic acid prepared by the hydrolysis of the ethyl ester by the procedure of Example 6 was suspended in 100 ml. of benzene. To this suspension was added 10 ml. of thionyl chloride. The resulting mixture was heated to refluxing temperature for two hours after which time the volatile constituents were removed by evaporation in vacuo. The residue, comprising 6,7-dichloro-3,4-dihydro-3-oxo-2-quinoxaline carboxyl chloride, was mixed with 50 ml. of isopropanol and the resulting mixture heated to refluxing temperature for 48 hours. Excess isopropanol was removed by evaporation in vacuo to yield 1.05 g. of isopropyl 6,7-dichloro-3,4-dihydro-3-oxo-2-quinoxaline carboxylate as a pale yellow solid which melted at 210°-211° C. after recrystallization from isopropanol.

Analysis Calc.: C, 47.86; H, 3.35; N, 9.30. Found: C, 48.16; H, 3.44; N, 9.28.

The corresponding allyl ester was prepared by the above procedure; melting point=228°-230° C. with decomposition.

Analysis Calc.: C, 48.19; H, 2.70; N, 9.37. Found: C, 47.89; H, 2.66; N, 9.42.

The corresponding n-butyl ester was prepared by the above procedure, and melted at 177°-178° C. after recrystallization from isopropanol.

Analysis Calc.: C, 49.54; H, 3.84; N, 8.89. Found: C, 50.56; H, 3.80; N, 8.94.

EXAMPLE 9

Preparation of Ethyl 6,7-dibromo-3,4-dihydro-3-oxoquinoxaline Carboxylate

Ten g. of 3,4-dibromoaniline were mixed with 40 ml. of acetic anhydride. The resulting reaction mixture was heated to a temperature in the range 100°-105° C. for one hour after which time it was poured over a mixture of ice and water. After stirring overnight, the aqueous mixture yielded an off-white precipitate weighing 11.5 g. and melting at 90°-95° C. comprising 3,4-dibromoacetanilide.

2.5 g. of 3,4-dibromoacetanilide were mixed with 8 ml. of 18 N aqueous sulfuric acid at 0° C. 1.5 g. of propyl nitrate were added while maintaining the reaction temperature in the range 0°-2° C. The chilled reaction mixture was stirred for one hour in the same temperature range and then poured over an ice-water mixture. A yellow solid comprising 4,5-dibromo-2-nitroacetanilide formed in the above reaction precipitated and was collected by filtration. Recrystallization from ethanol yields 1.2 g. of 3,4-dibromo-6-nitroacetanilide melting at 140°-141° C.

One gram of 4,5-dibromo-2-nitroacetanilide was heated to refluxing temperature for 30 minutes with 30 ml. of 6 N aqueous hydrochloric acid. The reaction mixture was then poured over an ice-water mixture and stirred. The pH of the solution was adjusted to 12 with alkali. The resulting bright yellow precipitate was separated by filtration, washed and dried; yield=0.85 g of 4,5-dibromo-2-nitroaniline melting at 204°-205° C.

Five grams of 4,5-dibromo-2-nitroaniline were suspended in 200 ml. of anhydrous ethanol to which was added about 10 g. of Raney Nickel. The hydrogenation mixture was placed in a low pressure hydrogenation apparatus at a hydrogen pressure of 55 psi. A rapid uptake of hydrogen occurred which ceased after about 25 minutes, at which time the deep yellow color originally present was discharged indicating complete reduction of the nitro group to an amine group. The hydrogenation was continued for another half hour and the hydrogenation mixture was then worked up by filtering off the catalyst, washing the filtered catalyst, and stripping the volatile constituents from the filtrate. A yield of 4.1 g. of 4,5-dibromo-o-phenylenediamine was obtained.

4,5-Dibromo-o-phenylenediamine was cyclized to the corresponding quinoxaline carboxylic acid ester by the procedure of Example 1 utilizing 4.1 g. of the diamine and 2.7 g. of diethyl ketomalonate in 75 ml. of anhydrous ethanol. Ethyl 6,7-dibromo-3,4-dihydro-3-oxo-2-quinoxaline carboxylate thus prepared melted at 235°-236° C. (yield=3.9 g.).

EXAMPLE 10

Preparation of Ethyl β-(6,7-dibromo-3,4-dihydro-3-oxo-2-quinoxaline)propionate Following the procedure of Example 9, 5 g. of 3,4-dibromo-6-nitroaniline were reduced in anhydrous ethanol with Raney nickel to yield 4,5-dibromo-o-phenylenediamine which was not isolated but mixed immediately with 2.47 g. of 2-ketoglutaric acid. One hundred ml. of ethanol were added and the mixture heated to refluxing temperature for 3 hours. 3 gms. of β-(6,7-dibromo-3,4-dihydro-3-oxo-2-quinoxaline)propionic acid were obtained melting at 249°-250° C. The free acid was converted to the corresponding ethyl ester by the procedure of Example 8. Ethyl β-(6,7-dibromo-3,4-dihydro-3-oxo-2-quinoxaline)propionate thus prepared melted at 189°-190° C.

Following the above procedure, 4,5-dichloro-o-phenylenediamine was reacted with 2-ketoglutaric acid in ethanol to yield 6,7-dichloro-3,4-dihydro-3-oxo-2-quinoxaline propionic acid. Reaction of the free acid with ethanol in the presence of $BF_3$ etherate yielded the corresponding ethyl ester, β-(6,7-dichloro-3,4-dihydro-3-oxo-2-quinoxaline)propionic acid, ethyl ester melting at 183.5-184.5. The free acid had the following analysis.

Analysis Calc.: C, 46.02; H, 2.81; N, 9.76. Found: C, 45.79; H, 2.53; N, 9.64.

EXAMPLE 11

Preparation of Ethyl 6(7)-Chloro-7(6)-bromo-3,4-dihydro-3-oxo-2-quinoxaline Carboxylate 3-Chloro-4-bromoacetanilide prepared by the procedure of Example 9 was nitrated in 18 M aqueous sulfuric acid with propyl nitrate at 0° C. according to the procedure of Example 9, The product of reaction was worked up by adding it to a mixture of ice and water with stirring. A yellow powder comprising 4-bromo-5-chloro-2-nitroacetanilide precipitated and was collected by filtration. Recrystallization from ethanol gave crystals melting at 128°-130° C.; yield=38 g.

4-Bromo-5-chloro-2-nitroacetanilide was hydrolyzed to the free amine by the process of Example 3. Reduction of 5 g. of 4-bromo-5-chloro-2-nitroaniline thus formed with Raney nickel by the procedure of Example 9 yielded 3.35 g. of 4-bromo-5-chloro-o-phenylenediamine. A 1.66 g. portion of the diamine were reacted with 0.85 g. of diethyl ketomalonate by refluxing in a mutual solvent for 2.5 hours. Yellow, needle-like crystals comprising ethyl 6(7)-chloro-7(6)-bromo-3,4-dihydro-3-oxo-2-quinoxaline carboxylate precipitated and were collected by filtration; mp=185°-195° C.; yield=1.11 g.

Following the above procedure, 4-nitro-o-phenylenediamine was reacted with diethyl ketomalonate to yield ethyl 6(7)-nitro-3,4-dihydro-3-oxo-2-quinoxaline carboxylate. The compound solidified after cooling. The solid was isolated by filtration and the filtercake washed with isopropanol. Yield=70 percent.

Analysis Calc.: C, 50.20; H, 3.45; N, 15.96. Found: C, 50.36; H, 3.50; N, 16.10.

EXAMPLE 12

Preparation of β-Chloroethyl 6,7-Dichloro-3,4-dihydro-3-oxo-2-quinoxaline Carboxylate 6,7-Dichloro-3,4-dihydro-3-oxo-2-quinoxaline carboxyl chloride was prepared according to the procedure of Example 8. The acid chloride (2.2 g.) was stirred with an excess of β-chloroethanol at 130° C. for 2 hours under a nitrogen atmosphere. Excess β-chloroethanol was removed by evaporation in vacuo at 50° C. The residue compound, β-chloroethyl 6,7-dichloro-3,4-dihydro-3-oxo-2-quinoxaline carboxylate was recrystallized from iso-propanol-acetone solvent mixture to yield 1.55 g. fluffy yellow flakes melting at 214°-215° C.

EXAMPLE 13

Preparation of Cyclobutylmethyl 6,7-Dichloro-3,4-dichloro-3-oxo-2-quinoxaline Carboxylate Five grams of 6,7-dichloro-3,4-dichloro-3-oxo-2-quinoxaline carboxylic acid prepared by the procedure of Example 6 were mixed with 25 g. of cyclobutanol and 5 ml. borontrifluoroetherate in a 50 ml. round bottom flask. The reaction mixture was refluxed at 140° C. for 2 hours with all starting material having dissolved. Thin layer chromatography showed that no starting material remained. On cooling lustrous yellowish-tan needles crystallized out. The reaction mixture was diluted with 25 ml. iso-propanol and refrigerated. The product, cyclobutylmethyl 6,7-dichloro-3,4-dichloro-3-oxo-2-quinoxaline carboxylate, was separated out by filtration and washed once with 25 ml. hexane to yield 3.55 g. with the melting point, 183°-184° C.

EXAMPLE 14

Preparation of Ethyl 6-Nitro-8-chloro-3,4-dihydro-3-oxo-2-quinoxaline carboxylate and Ethyl 7-Nitro-5-chloro-3,4-dihydro-3-oxo-2-quinoxaline Carboxylate 3-Chloro-5-nitro-o-phenylenediamine (1.87 g.) was dissolved in 15 ml. of anhydrous ethanol. The solution was heated to refluxing temperature for 24 hours. The volatile constituents were removed by evaporation in vacuo. Recrystallization of the residue from an ethanol solution yielded the mixture of ethyl 6-nitro-8-chloro-3,4-dihydro-3-oxo-2-quinoxaline carboxylate and its isomer ethyl 5-chloro-7-nitro-3,4-dihydro-3-oxo-2-quinoxaline carboxylate.

EXAMPLE 15

Preparation of Ethyl 6-methoxy-5-nitro-3,4-dihydro-3-oxo-2-quinoxaline Carboxylate and Ethyl 7-Methoxy-8-nitro-3,4-dihydro-3-oxo-2-quinoxaline Carboxylate 3-Nitro-5-methoxy-o-phenylenediamine (1.83 g.) was dissolved in 25 ml. of anhydrous ethanol and 1.8 g. of diethyl ketomalonate was added. The mixture was refluxed for 48 hours. The volatile constituents were evaporated in vacuo. The residue was recrystallized from a propanol-ethanol solution yielding 2.2 g. of the mixture of ethyl 6-methoxy-8-nitro-3,4-dihydro-3-oxo-2-quinoxaline carboxylate and its isomer ethyl 7-methoxy-5-nitro-3,4-dihydro-3-oxo-2-quinoxaline carboxylate.

Table 1 below lists compounds prepared by one of the above reaction procedures. The table gives the particular substituent groups, indicates whether the compound was prepared in pure form or as a mixture of isomers, and gives the elemental analysis (calculated and found) for each compound. In addition, a letter had been assigned to each compound in order to facilitate the reading of the test results in subsequent tables.

TABLE 1

| Compound | R, $R^4$ | $R^1$ | $R^2$ | $R^3$ | n | ANALYSIS CALC. C | H | N | ANALYSIS FOUND C | H | N |
|---|---|---|---|---|---|---|---|---|---|---|---|
| A | H | $NO_2$ | H | Et | 0 | 50.20 | 3.45 | 15.96 | 50.36 | 3.50 | 16.10 |
|   | H | H | $NO_2$ | Et | 0 |  |  |  |  |  |  |
| B | H | Cl | Cl | H | 2 | 46.02 | 2.81 | 9.76 | 45.79 | 2.53 | 9.64 |
| C | H | Cl | Cl | Me | 0 | 43.98 | 2.21 | 10.26 | 44.24 | 2.15 | 10.50 |
| D | H | Cl | Cl | Et | 0 | 46.02 | 2.81 | 9.76 | 46.15 | 2.99 | 9.95 |
| E | H | Cl | Cl | H | 0 | 41.73 | 1.56 | 10.81 | 41.44 | 1.67 | 10.80 |
| F | H | I | I | Et | 0 | 28.09 | 1.70 | 5.96 | 28.01 | 1.72 | 6.07 |
| G | H | Cl | Cl | n-Bu | 0 | 49.54 | 3.84 | 8.89 | 50.56 | 3.93 | 8.95 |
| H | H | F | F | Et | 0 | 51.98 | 3.17 | 11.02 | 51.98 | 3.32 | 10.86 |
| I | H | Cl | Cl | isoPr | 0 | 47.86 | 3.35 | 9.30 | 48.16 | 3.44 | 9.28 |
| J | H | Cl | Cl | β-Cl—Et | 0 | 41.06 | 2.18 | 8.71 | 41.80 | 2.29 | 8.65 |
| K | H | Cl | Cl | allyl | 0 | 48.19 | 2.70 | 9.32 | 47.89 | 2.66 | 9.42 |
| L | H | Cl | Cl | cyclobutyl- | 0 | 51.40 | 3.70 | 8.56 | 51.17 | 3.69 | 8.83 |

TABLE 1-continued

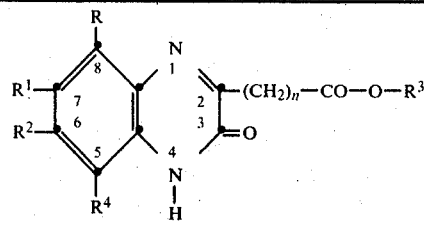

| Compound | R, R⁴ | R¹ | R² | R³ | n | \multicolumn{3}{c}{ANALYSIS CALC.} | \multicolumn{3}{c}{ANALYSIS FOUND} |

| Compound | R, R⁴ | R¹ | R² | R³ | n | C | H | N | C | H | N |
|---|---|---|---|---|---|---|---|---|---|---|---|
| M | H | Br | Br | methyl Et | 0 | 35.14 | 2.14 | 7.45 | 35.40 | 2.36 | 4.56 |
| N | H | Br | Br | Et | 2 | 38.61 | 2.97 | 6.93 | 38.85 | 3.16 | 6.18 |
| O | H | Cl | Cl | Et | 2 | 49.52 | 3.81 | 8.89 | 49.37 | 3.63 | 8.83 |
| P | H | Br | Br | H | 2 | 35.11 | 2.13 | 7.45 | 35.35 | 1.95 | 7.60 |
| Q | H | Br | Cl | Et | 0 | 39.85 | 2.43 | 8.45 | 39.43 | 2.59 | 8.52 |
|   | H | Cl | Br | Et | 0 |   |   |   |   |   |   |
| R | NO₂ | MeO | H | Et | 0 | 49.15 | 3.78 | 16.33 | 48.97 | 3.74 | 14.06 |
|   | NO₂* | H | MeO | Et | 0 |   |   |   |   |   |   |
| S | Cl | H | NO₂ | Et | 0 | 44.32 | 2.69 | 14.12 | 44.71 | 2.86 | 14.07 |
|   | Cl* | NO₂ | H | Et | 0 |   |   |   |   |   |   |

*5-substituent (R⁴)

The compounds represented by Formulas I, II, III or X above are active both in vitro and in vivo against two different strains of influenza virus, Maryland B and Ann Arbor. In vitro antiviral activity was determined as follows:

African green monkey kidney cells (BSC-1) or Hela cells (5-3) were grown in 25 cc. Falcon flasks at 37° C. in medium 199 with 5 percent inactivated fetal bovine serum (FBS), penicillin (150 units 1 ml.) and streptomycin (150 mcg./ml.). When confluent monolayers were formed, the supernatant growth medium was removed and 0.3 ml. of an appropriate dilution of Maryland B or Ann Arbor influenza virus was added to each flask. After adsorption for one hour at room temperature, the virus infected cell sheet was overlaid with a medium comprising one part 1 percent Ionagar No. 2 and one part double strength medium 199 with FCS (fetal calf serum), penicillin, and streptomycin and also containing drug at concentrations of 100, 50, 25, 12, 6 and 3 micrograms per milliliter (mcg./ml.). The flask containing no drug served as a control. The stock solutions of the quinoxalinone compounds were made up in dimethylsulfoxide dilution at a concentration of $10^4$ mcg./ml. The flasks were incubated for 72 hours at 37° C. Plaques were seen in those areas where the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the compound was expressed as percentage plaque inhibition. In Table 2 which follows, column 1 gives the letter assigned to the compound, and columns 2 and 4 the $I_{50}$, amount of drug in mcg/ml which inhibits 50% of the plaques.

In vivo activity was determined as follows: White Swiss female mice (11-13 g.) McAllister strain were infected with aqueous dilutions of Ann Arbor or Maryland B strains of influenza virus in an air borne injection apparatus. Graded dose levels of the drug were injected intraperitoneally (IP) or administered orally by gavage 24 and 4 hours preinfection and 24 and 48 hours postinfection. Date of death was determined. The drug was administered in water containing 2% of a surfactant. In Table 1, column 7, a dosage level for each drug is given at which there was a statistically significant increase in survival and column 6 gives the route of administration.

TABLE 2

| Compound | Maryland B Influenza Virus in vitro $I_{50}$ | Ann Arbor Influenza Virus in vitro $I_{50}$ | Route | in vivo dose mg/kg |
|---|---|---|---|---|
| A | 40 |   | IP | 80 |
| B |   |   | IP | 50 |
| C | <10 |   | IP | 60 |
| D | 38 |   | IP, OR | 40 |
| E | <71 | <100 | IP | 50 |
| F |   | Active |   | 80 |
| G | 38 |   |   |   |
| H | 5 < 10 |   |   |   |
| I |   |   |   |   |
| J | 58 | 76 |   |   |
| K | 33 | 75 |   |   |
| L | 15 | 20 |   |   |
| M |   |   | IP, OR | 40-80 |
| Q |   |   | IP | 80 |
| R |   |   | IP | 80 |
| S |   |   | IP | 80 |

The compounds represented by Formulas I, II, III or X have also shown activity in vitro against other viruses in a plaque suppression test similar to that used in determining activity against Maryland B or Ann Arbor influenza virus. Table 3 which follows summarizes the results of these tests. In the table, column 1 gives the alphabetic symbol for the compound, column 2 the virus against which the compound was tested and column 3, the dose level in micrograms per ml. at which activity was found.

TABLE 3

| Compound Symbol | Virus | Activity level in mcg/mg |
|---|---|---|
| A | Vaccinia | 2000 |
| C | Echo 10 | 2000 |
|   | Coxsackie A-21 | 2000 |
| D | Semliki Forest | 2000 |
|   | Polio III | 1000-2000 |
|   | Vaccinia | 2000 |
|   | Herpes simplex | 1000-2000 |

TABLE 3-continued

| Compound Symbol | Virus | Activity level in mcg/mg |
|---|---|---|
| G | Echo 10 | 2000 |
| H | Vaccinia | 2000 |
|  | Polio III | 2000 |
| I | Semliki Forest | 2000 |
|  | Vaccinia | 2000 |
|  | Herpes simplex | 2000 |
| J | Vaccinia | 2000 |
| L | Echo 10 | 2000 |
|  | Vaccinia | 2000 |
|  | Herpes simplex | 2000 |
| M | Echo 10 | 2000 |
| N | Echo 10 | 2000 |
|  | Herpes simplex | 2000 |
| O | Herpes simplex | 2000 |
|  | Echo 10 | 2000 |
| P | Echo 10 | 2000 |
| Q | Vaccinia | 2000 |
|  | Polio III | 2000 |
|  | Vaccinia | 2000 |
| R | Herpes simplex | 2000 |
|  | Echo 10 | 2000 |
| S | Echo 10 | 2000 |
|  | Vaccinia | 2000 |
|  | Herpes simplex | 2000 |

Quinoxaline-2-carboxylates, according to formulas I, II, III or X above, have been shown by the above tables to have both in vivo and in vitro activity against influenza virus, both A and B strains, and to have in vitro activity against other viruses. For in vitro use, the compounds can be formulated by dissolving them in a lower alkanol, for example ethanol or methanol, or at low concentration as an emulsion in water with the use of a surface active agent. If $R^3$ in formula I is H, an alkali metal salt of the acid can be used in aqueous solution. The antiviral composition containing a quinoxaline according to formula I as the active ingredient is, therefore, applied to the virus habitat in vitro, such habitats including walls of hospital rooms, laboratory benches, laboratory glassware, and the like. The compounds can also be added to tissue culture to suppress viral growth therein. For in vivo use, the compounds can be administered either parenterally or orally. For parenteral administration, as by the intraperitoneal route employed in the above experimental work, the compound may be dissolved in water containing 2% of a surface active agent, particularly an emulphor (a polyhydroxylated fatty acid). Oral administration is, of course, preferred. For such use, a quinoxaline according to formula I above is mixed with one or more standard pharmaceutically-acceptable extending media such as starch, sucrose, lactose, calcium carbonate etc. and the mixture loaded into empty telescoping gelatin capsules, such that each capsule contains an amount of a quinoxaline effective to suppress the growth of influenza virus, either prospective or present. In other words, the compounds can be used prophylactically or as curative agents. Alternatively, the drug can be mixed with various excipients including starch, lubricating agents, wetting agents, etc., such as stearic acid, magnesium sterate and the like, and the mixture pressed into tablets, each tablet containing an amount of the drug effective to abort or cure an attack of influenza. Such tablets can be scored so as to provide half or quarter dosages where the drug is to be administered to children. The compounds can also be administered in solution or suspension.

Compounds represented by one or more of formulae I, II, III and X above are administered to mammals susceptible to infection with influenza virus including horses, mice, pigs and humans. Among humans, the compounds are administered prophylactically particularly to the elderly, young children, nurses, doctors, and other hospital or public health personnel, when there is evidence of an imminent "flu" epidemic. The compounds can also be given to anyone having a known exposure to a person with "flu". It is a particular advantage of the therapeutic processes of this invention that the compounds may be administered either prophylactically or therapeutically to patients without a preliminary determination that the virus is influenza virus A strain or B strain, since the compounds are effective against both strains.

As previously stated, ethyl 6,7-dichloro-3,4-dihydro-3-oxo-2-quinoxalinecarboxylate has been used as an intermediate in the production of diethylaminoalkylamino quinoxalines and of azeto[1,2-a]quinoxaline-1,3-diones. Other halogenated derivatives of 3,4-dihydro-3-oxo-2-quinoxaline carboxylic acid and its esters are not known. Surprisingly, one of these, ethyl 6,7-dibromo-3,4-dihydro-3-oxo-2-quinoxaline carboxylate is much less toxic in monkeys than its 6,7-dichloro congener. Ethyl 6,7-dibromo-3,4-dihydro-3-oxo-2-quinoxaline carboxylate was given to male and female monkey treatment groups by oral gavage at the rate of 90 mg/day for 14 days. Several clinical parameters were measured. No dramatic changes in alkaline phosphatase (AP) or serum glutamic-pyruvic transaminase (SGPT), both indicators of hepatotoxicity, were seen. Dosages were raised to 120 mg/day for 14 additional days. Clinical parameters were measured at the end of this period and 14 days after termination. Again there were no dramatic changes in AP or SGPT values. By contrast, administration of ethyl 6,7-dichloro-3,4-dihydro-3-oxo-2-quinoxaline carboxylate at a 30 mg/day rate to female rhesus monkeys by nasogastric gavage for 14 days gave moderate increases in AP and SGPT, suggestive of liver damage. Increasing the dosage to 60 mg/day for only 7 days caused AP to remain elevated but SGPT returned to normal. There was also evidence of kidney damage in these monkeys, wih an elevated blood urea nitrogen and creatinine levels. Administration of both drugs to groups of rats (100 mg/kg) or dogs (30–60 mg/kg) however, showed equal, though minor, degrees of nephrotoxicity and hepatotoxicity.

I claim:

1. A method for suppressing an influenza viral infection in mammals which comprises administering to a mammal susceptible to infection by influenza virus a dose effective to suppress the growth of influenza virus of a compound of the formula:

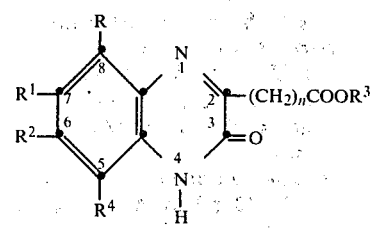

wherein R and $R^4$ are individually H or $NO_2$; $R_1$ and $R^2$ are individually H, $NO_2$, MeO or halo such that at least one of R, $R^1$, $R^2$ and $R^4$ is other than H, such that if neither $R^1$ and $R^2$ is $NO_2$ or MeO, both $R^1$ and $R^2$ are individually halo and both R and $R^4$ are H, and such that one of $R^1$ and $R^2$ is MeO only if one of R, $R^1$, $R^2$ and $R^4$ is nitro; $R^3$ is $C_1$–$C_4$ alkyl, $C_3$–$C_6$ cycloalkyl, $C_3$–$C_4$ alkenyl, H or 2-chloroethyl; and n is 0 or 2.

2. A method according to claim 1 in which the influenza virus is an A-strain virus.

3. A method according to claim 1 in which the influenza virus is a B-strain virus.

4. A method according to claim 1 in which a compound of the formula below is used to suppress the growth of influenza virus:

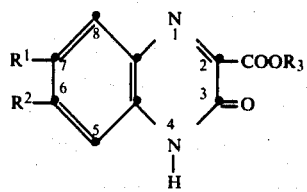

wherein $R^1$ and $R^2$ are individually halogen or nitro but only one is nitro; and $R^3$ is H, $C_1$–$C_4$ alkyl, $C_3$–$C_6$ cycloalkyl, $C_3$–$C_4$ alkenyl or 2-chloroethyl.

5. A method according to claim 4 in which a compound of the formula below is used to suppress the growth of influenza virus:

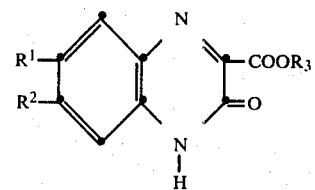

wherein $R^1$ and $R^2$ are separately Cl, Br, F or I and $R^3$ is $C_1$–$C_4$ alkyl.

6. A method according to claim 5 in which the antiviral compound is ethyl 6,7-dibromo-3,4-dihydro-3-oxo-2-quinoxaline carboxylate.

7. A method according to claim 5 in which the antiviral compound is methyl 6,7-dichloro-3,4-dihydro-3-oxo-2-quinoxaline carboxylate.

8. A method according to claim 5 in which the antiviral compound is ethyl 6,7-dichloro-3,4-dihydro-3-oxo-2-quinoxaline carboxylate.

9. A method for suppressing viral growth which comprises applying to an in vitro viral habitat a growth suppressing amount of a compound of the formula

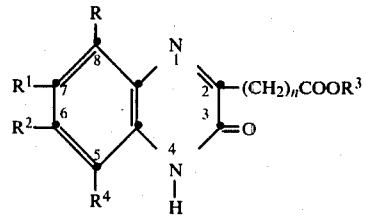

wherein R and $R^4$ are individually $H_1$ or $NO_2$; $R_1$ and $R^2$ are individually H, $NO_2$, MeO or halo such that at least one of R, $R^1$, $R^2$ and $R^4$ is other than H, such that if neither $R^1$ and $R^2$ is $NO_2$ or MeO, both $R^1$ and $R^2$ are individually halo and both R and $R^4$ are H, and such that one of $R^1$ and $R^2$ is MeO only if one of R, $R^1$, $R^2$ and $R^4$ is nitro; $R^3$ is $C_1$–$C_4$ alkyl, $C_3$–$C_6$ cycloalkyl, $C_3$–$C_4$ alkenyl, H or 2-chloroethyl; and n is 0 or 2.

* * * * *